US012317928B2

(12) United States Patent
Bergmann et al.

(10) Patent No.: US 12,317,928 B2
(45) Date of Patent: Jun. 3, 2025

(54) VAPORIZER CARTRIDGE AND INHALER COMPRISING SUCH A VAPORIZER CARTRIDGE

(71) Applicant: KÖRBER TECHNOLOGIES GMBH, Hamburg (DE)

(72) Inventors: Max Bergmann, Hamburg (DE); Lasse Cornils, Hamburg (DE); Matthias Giese, Tokyo (JP); Christian Hanneken, Hamburg (DE); Jan Jaklin, Fellbach (DE); Marc Kessler, Hamburg (DE); Michael Kleine Wächter, Lankau (DE); Thomas Müller, Hamburg (DE); Niklas Romming, Hamburg (DE); Christof Schuster, Hamburg (DE); Tobias Wuttke, Reinbek (DE); Rene Schmidt, Buchholz i.d.N. (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 633 days.

(21) Appl. No.: 17/619,389

(22) PCT Filed: Jun. 17, 2020

(86) PCT No.: PCT/EP2020/066737
§ 371 (c)(1),
(2) Date: Dec. 15, 2021

(87) PCT Pub. No.: WO2020/254390
PCT Pub. Date: Dec. 24, 2020

(65) Prior Publication Data
US 2022/0361572 A1 Nov. 17, 2022

(30) Foreign Application Priority Data
Jun. 20, 2019 (DE) .......................... 102019116728.0

(51) Int. Cl.
A24F 40/42 (2020.01)
A24F 40/10 (2020.01)
(Continued)

(52) U.S. Cl.
CPC .............. *A24F 40/42* (2020.01); *A24F 40/10* (2020.01); *A24F 40/44* (2020.01); *A24F 40/46* (2020.01); *A24F 40/485* (2020.01)

(58) Field of Classification Search
None
See application file for complete search history.

(56) References Cited

U.S. PATENT DOCUMENTS 11,958,068 B2 * 4/2024 Pelz ...................... B05B 7/0884
2014/0238424 A1 * 8/2014 Macko ..................... A24F 40/44
131/328

(Continued)

FOREIGN PATENT DOCUMENTS

DE 102017123870 A1 4/2019
EP 3200559 A2 8/2017

(Continued)

OTHER PUBLICATIONS

International Search Report dated Oct. 8, 2020; International Application PCT/EP2020/066737.

*Primary Examiner* — Philip Y Louie
*Assistant Examiner* — Eric M Fierce
(74) *Attorney, Agent, or Firm* — Dinsmore & Shohl LLP

(57) ABSTRACT

A vaporizer cartridge, as a component of an inhaler, has a hollow body with a continuous flow channel and a storage tank for storing liquid. The storage tank has at least one access opening to the flow channel and a vaporizer unit arranged in the region of the access opening and extending over the entire access opening. The vaporizer unit has a wick member and a heating member. The vaporizer unit is formed (Continued)

to be liquid-permeable such that liquid can be conveyed at least initially in a capillary manner out of the storage tank through the vaporizer unit in the direction of the flow channel. The wick member is formed from a plurality of granular grains which form microchannels as a result of their fill and/or formation. An inhaler is also provided.

21 Claims, 8 Drawing Sheets

(51) Int. Cl.
*A24F 40/44* (2020.01)
*A24F 40/46* (2020.01)
*A24F 40/485* (2020.01)
*A61M 15/06* (2006.01)

(56) References Cited

U.S. PATENT DOCUMENTS

2014/0299125 A1* 10/2014 Buchberger ............ A24F 40/46
514/343
2016/0316819 A1 11/2016 Zhou et al.
2017/0367411 A1 12/2017 Duc
2021/0186097 A1 6/2021 Schmidt et al.

FOREIGN PATENT DOCUMENTS

| EP | 3417726 A1 | 12/2018 |
| GB | 2561867 A | 10/2018 |
| WO | 2013083638 A1 | 6/2013 |
| WO | 2018211035 A1 | 11/2018 |

* cited by examiner

VAPORIZER CARTRIDGE AND INHALER COMPRISING SUCH A VAPORIZER CARTRIDGE

CROSS-REFERENCE TO RELATED APPLICATIONS

This application is the U.S. National Stage of PCT/EP2020/066737 filed Jun. 17, 2020, which claims priority to German Patent Application No. 102019116728.0, filed Jun. 20, 2019, the content of both are incorporated herein by reference in their entirety.

FIELD OF THE INVENTION

The invention relates to a vaporizer cartridge as a component of an inhaler, comprising a hollow body with a continuous flow channel as well as a storage tank for storing liquid, wherein the storage tank has at least one access opening to the flow channel, and a vaporizer unit extending over the entire access opening is arranged in the region of each access opening and has a wick member and a heating member, wherein the vaporizer unit is formed to be liquid-permeable such that liquid can be conveyed at least initially in a capillary manner out of the storage tank through the vaporizer unit in the direction of the flow channel.

The invention furthermore relates to an inhaler, configured and adapted for the inhalation of vapour enriched with active ingredients, comprising a cartridge carrier at least comprising an electronic control unit and an energy source as well as a vaporizer cartridge.

BACKGROUND OF THE INVENTION

Such vaporizer cartridges and inhalers are used in the luxury goods/stimulants industry, here in particular in the context of an electronic cigarette, what is known as an E-cigarette, and in the medical sector in order to be able to inhale liquid beverages and tobacco and/or liquid medical products in vapour form and/or as aerosols. During consumption, a person normally sucks on a mouthpiece of the inhaler, as a result of which a suction pressure arises in an air flow channel, which suction pressure generates an air flow through the air flow channel. The air flow can, however, also be generated by machine, for example, by a pump. In the air flow channel, a liquid which is generated by the vaporizer unit and provided in a vaporized form is added to the air flow in order to administer an aerosol or an aerosol-vapour mixture to the consuming person. The liquid is stored at or in the vaporizer cartridge. Various mixtures with various components of the same or different vapour densities are used as the liquid. A typical mixture for use in an E-cigarette has, for example, components of glycerine and propylene glycol, where applicable, enriched with nicotine and/or almost any desired flavouring agents. The mixture can correspondingly have medical components and active ingredients for use in the medical or therapeutic sector, i.e. for the inhalation of asthma preparations.

The individual components of the vaporizer cartridge, namely the hollow body, the storage tank and the vaporizer unit can be combined in a joint component, wherein this component is a single-use article which is designed for a finite number of inhalations by a consuming person and together with a cartridge carrier as a reusable multi-use article which comprises at least one electronic control unit and an energy source forms an inhaler. The vaporizer cartridge can, however, also only be formed by the joining together of several components, wherein individual components, namely in particular the hollow body and the vaporizer unit, are arranged in the cartridge carrier as a multi-use article, and the storage tank as a separate component forms the single-use article. Finally, the inhaler can be used variably by replacing the single-use article which normally contains the liquid.

The single-use article and the multi-use article are correspondingly connected detachably to one another. The cartridge carrier as a reusable article normally comprises at least one electronic control unit and an energy source. The energy source can be e.g. an electrochemical single-use battery or a rechargeable electrochemical battery, e.g. a Li-ion battery by means of which the heating member is supplied with energy via electrical contacts of the vaporizer unit. The electronic and/or electrical control unit serves to control the vaporizer unit within the vaporizer cartridge. The cartridge carrier can, however, also comprise components of the vaporizer cartridge. The single-use article can be formed so as to be capable of being plugged as a plug-on part onto the multi-use article or inserted as an insertion part into the multi-use article. Instead of a plug-type connection, screw connections, snap connections or other quick connections can also be used. A mechanical and electrical coupling for the formation of a functionally ready inhaler is produced with the connection of single-use article and multi-use article.

The central component which ultimately determines the use (e.g. as an E-cigarette or as a medical inhaler) is the storage tank as a component of the vaporizer cartridge. This generally contains the liquid selected, desired and/or required by the person or a liquid mixture (also referred to generally below as fluid) as well as the hollow body that forms the flow channel and the vaporizer unit. The fluid is stored in the storage tank of the vaporizer cartridge. The fluid is conveyed by means of the liquid-permeable vaporizer unit out of the storage tank as a result of at least initially capillary conveyance through the wick member and the heating member. The voltage generated by an energy source which is applied to the heating member leads to a flow of current in the heating member. As a result of the heating resistance, preferably the ohmic resistance of the heating member, the flow of current leads to a heating of the heating member and ultimately to a vaporization of the fluid located in the vaporizer unit. The vapour and/or aerosol generated in this manner escapes from the vaporizer unit in the direction of the flow channel and is mixed with the air flow as added vapour. The fluid thus has a predefined path with a predefined direction of flow, namely as fluid through the wick member to the and through the heating member and in gaseous form out of the heating member into the flow channel. In the flow channel, the vaporized fluid is carried along by the air flow, wherein vapour/mist and/or aerosol forms if a pressure/vacuum acts on the flow channel, by virtue of the fact that e.g. a consuming person sucks on the flow channel or a pump conveys an air flow through the flow channel.

So that the fluid does not flow directly out of the storage tank into the flow channel, the vaporizer unit entirely covers the access from the storage tank to the flow channel. Entirely covers means in this context that the liquid is necessarily guided through the vaporizer unit so that the fluid cannot travel directly from the storage tank into the flow channel, but rather must take the "detour" via the wick member and the heating member. The wick member serves on the one hand the purpose of intermediate storage of fluid in order to still make available sufficient fluid for a few draws on the inhaler in particular in the case of an almost empty storage tank. The wick member serves on the other hand in particular the purpose of transporting the fluid from the storage tank in the direction of the flow channel and acts simultaneously as a type of non-return protection in order to prohibit the return flow of fluid and/or gas or vapour in the direction of the storage tank and prevent an enrichment of individual components of the fluid at higher temperatures.

Hitherto known vaporizer cartridges have a vaporizer unit with a wick member which is formed from several threads/fibres which are interwoven/twisted with one another composed e.g. of cotton wool or glass fibres. This fibre wick has capillary properties which lead, upon initial contact with the fluid, to the fibre wick dipping into the storage tank, and the fluid in the storage tank being absorbed and conveyed in the direction of the heating member. The heating member is normally formed in the form of a spiral-wound filament. This wound metal wire is composed, for example, of stainless steel, copper, copper compounds or nickel. This vaporizer unit can generally only be produced manually and has a limited storage capacity for intermediate storage of fluid. A further disadvantage lies in the low transport rate of fluid as a result of the limited number of microchannels. A non-homogeneous and uncontrollable temperature distribution furthermore arises along the wick-spiral coil system. In other words, a uniform and continuous supply of the heating member with the fluid is only ensured to a limited extent. There is furthermore the risk of local overheating with the consequence of the generation of pollutants. This solution furthermore does not have any non-return protection.

In the case of other known solutions, the vaporizer unit therefore comprises a one-piece wick block as the wick member. This wick block normally composed of ceramic materials simplifies the automated production of the vaporizer unit and the vaporizer cartridge and has several microchannels for a transport rate which is increased in comparison with the fibre wick. Nevertheless, this solution also has several disadvantages. In addition to a still limited transport rate and intermediate storage capacity, the use of such block-like wick blocks is very inflexible and above all difficult to mount since the wick blocks can only be used in exactly prefabricated—in a narrow tolerance range—receivers/holders or the like.

In the case of a one-piece wick body, this itself can serve as a heating member if the e.g. ceramic material of the wick body which has microchannels is formed to be electrically conductive. The wick body then has a dual function and forms the vaporizer unit. In other cases, in addition to the wick body, a separate component can serve as a heating member. In the latter case, the wick body and the separate heating member form the vaporizer unit. The heating member is then normally a laminar and flat MEMS component (Micro-electro-mechanical-system component) which is composed e.g. substantially of silicon or has silicon or p- or n-doped silicon and which is formed to be liquid-permeable. The above-mentioned disadvantages are amplified in particular in the case of solutions in which wick member and heating member are separate bodies which bear against one another in a contact region.

A further disadvantage arises in that different surface roughnesses lie on top of one another in the contact region, namely on the one hand the porous structure of the wick member and on the other hand the normally smooth surface of the heating member. Undefined cavities which do not form microchannels arise in the contact region as a result of the different roughnesses. These cavities lead to an inadequate fluid supply of the heating member with the fluid. In other words, such cavities hinder an adequate fluid coupling between the exit side of the wick member and the entry side of the heating member. Further cavities arise as a result of a non-plane-parallel orientation of the surfaces of wick member and heating member, e.g. as a result of arched surfaces and/or mounting errors. This leads to inadequate reproducibility of the mounting results, as a result of which fluctuating vaporizing conditions are produced. The existing cavities can lead to a thermally insulating vapour bubble formation, what is known as the Leidenfrost effect, with the undesired effect of (local) overheating. Moreover, vapour bubbles hinder the subsequent conveyance of the fluid out of the wick member into the heating member.

SUMMARY OF THE INVENTION

The object on which the invention is based is thus to propose a compact vaporizer cartridge which ensures constant and reproducible vaporizing conditions. The object furthermore lies in creating a corresponding inhaler.

This object is achieved by a vaporizer cartridge of the above-mentioned type in that the wick member is formed from a plurality of granular grains which, as a result of their fill and/or formation, form microchannels. The term fill describes the grains lying next to one another both loosely and in a connected manner, wherein shaken and/or compressed arrangements of the grains are also covered by this term. The term formation of the grains describes, for example, that the grains themselves can have micro-cavities and/or microchannels. A plurality of random microchannels between the storage tank and the flow channel which ensure a constant and uniform vaporization on the exit side of the vaporizer unit are thus formed in the vaporizer unit between the individual grains which lie against one another and/or by individual grains. In other words, an optimum fluid coupling between the entry side into the vaporizer unit and the exit side out of the vaporizer unit is established by the granular wick member. A wide range of advantages are achieved in comparison with the solutions known from the prior art with the configuration according to the invention of the wick member. In addition to the improved transport rate, more fluid and above all fluid is conducted in a uniform manner from the storage tank through the vaporizer unit, the granular wick member ensures an increased intermediate storage capacity for fluid as a result of the granular and thus porous wick structure. A granular wick member furthermore improves the non-return protection since the formed microchannels have a non-linear profile. The mounting of a granular wick member is particularly advantageous since this can be adapted at the respective mounting location to any desired contour/geometry of the receiver of the wick member. As a result of the grain structure, the wick member adapts during mounting/filling of the granular material flexibly to the respective contour/geometry and fills undesirable cavities which do not form microchannels—with the formation of microchannels and/or micro-cavities—and avoids the formation of gaps to adjoining surfaces. As a result, constant and reproducible vaporization conditions are ensured by the granular wick member. It does not play any role here whether the vaporizer unit—with the wick member and/or the heating member as a component of the vaporizer cartridge—is arranged on or in the cartridge carrier, i.e. on/in the multi-use article, or whether the vaporizer unit is arranged on/in the single-use article.

The microchannels of the wick member, irrespective of whether it only has the wick function or a combined wick and heating function, extend continuously from an entry side $E_D$ to an exit side $A_D$ so that fluid is transported either from the storage tank through the wick member in the direction of the flow channel and thereby heated so that gaseous liquid/vapour is transported out of the wick member into the flow channel, or fluid is transported from the storage tank to the heating member which is liquid- and vapour-permeable and generates vapour from the fluid, which vapour is transported from the heating member into the flow channel.

The vaporizer cartridge can on the one hand be formed in that a storage tank as a component of the vaporizer cartridge as a single-use article is connected to at least one cartridge carrier as a multi-use article which comprises, in addition to a control unit and an energy source, e.g. the vaporizer unit as a component of the vaporizer cartridge. On the other hand, the vaporizer cartridge can be a unit formed at least from vaporizer unit and storage tank as a single-use article which is configured and adapted for mechanical and electrical connection to at least one cartridge carrier at least comprising an electronic control unit and an energy source as a multi-use article for the formation of an inhaler, wherein the vaporizer unit comprises electrical contacts for electrical contact with the energy source. As a result of this, compact vaporizer cartridges/inhalers with constant and reproducible vaporizing conditions are created.

One expedient further development is characterised in that the granulosus material which forms the granular wick member is at least partially electrically conductive. The wick member thus advantageously also forms the heating member. The vaporizer unit is correspondingly a single member, i.e. formed quasi "in one piece", as a result of which a particularly compact design is achieved. The fluid coupling between wick member and heating member is optimal in the case of this variant since the microchannels are formed without interruption and continuously from the entry side into the vaporizer unit up to the exit side out of the vaporizer unit.

In one preferred embodiment, a receiving chamber for receiving the vaporizer unit is formed in the region of the access opening, wherein the receiving chamber for receiving liquid from the storage tank into the vaporizer unit and to discharge gaseous liquid/vapour from the vaporizer unit into the flow channel is at least partially delimited by a liquid- and gas- or vapour-permeable structure. The receiving chamber for the vaporizer unit can be formed by housing walls, projections, plates, covers, coil elements, valves or any other restriction or combinations thereof. It is vital that at least one liquid- and vapour-permeable access from the storage tank and at least one liquid- and gas- or vapour-permeable outlet to the flow channel exist. The receiving chamber holds the wick member and the heating member together and in position, and indeed in front of the access opening between storage tank and flow channel, so that the liquid on the one hand is reliably prevented from flowing directly out of the storage tank into the flow channel, and on the other hand is conducted in a uniform manner and constantly in the direction of the flow channel. As a result of the surface of the outlet to the flow channel and the access to the storage tank, the partial pressure above the wick member can be adjusted.

In one advantageous further development, the vaporizer cartridge comprises a carrier element which forms the hollow body and on the one hand has a through-opening for forming the flow channel and on the other hand has a recess for receiving the vaporizer unit. A particularly compact vaporizer cartridge is created with this formation.

A sediment formed from the granular and electrically conductive material is advantageously fixed such that the sediment forms a three-dimensional resistance heating matrix with parallel resistors and/or resistors connected in series. In addition to the wick function of the capillary fluid transport, the wick member can thus also be used particularly effectively as a heating member for defined and reproducible vaporizing conditions. The electrically conducting wick member can be electrically linked, for example, via press contacts, wherein at least two contacts are required.

The grains of the wick member are preferably formed to be identical and/or non-identical in terms of their material selection and/or their size. This means that grains within a wick member are all composed of the same material and are all of the same size (this means an order of magnitude within a defined range), or all the grains are composed of one material but are of a different size, or the grains are composed of different materials, but are of the same size, or the grains are composed of different materials and are of a different size. Wick members can thus be assembled in a simple and individual manner e.g. for different liquids and liquid mixtures e.g. with different transport rates (liquid supply) and/or different thermal conductivities and/or different flow resistances (e.g. for an adapted non-return protection).

One preferred embodiment is characterised in that the grains of the wick member, proceeding from the storage tank in the direction of the flow channel, have locally different grain sizes. For example, the grains can vary by layer in terms of their size. This layered structure can still be performed flexibly during mounting/filling in order to adjust e.g. the flow gradient in the granular wick member.

The grains of the wick member, proceeding from the storage tank in the direction of the flow channel, are advantageously composed locally of different materials. With the layered change in the material of the grains, for example, a changeable thermal conductivity of the wick member can be achieved in that materials with low thermal conductivity can be used e.g. on the side of the wick member facing the storage tank in order to avoid e.g. a heat transfer to the liquid located in the storage tank, while materials with high thermal conductivity are used on the side of the wick member facing the flow channel in order to support the vaporization process in the direction of the flow channel or keep the heat in the transition region to the flow channel.

The grains of the wick member preferably lie as loose fill within the receiving chamber. In the case of this variant, a particularly uniform and above all cavity- and gap-reduced distribution of the grains within the receiving chamber is ensured, as a result of which constant and reproducible vaporizing conditions are further optimized.

In another advantageous variant, the grains of the wick member lie as fill connected to one another within the receiving chamber. The connection of the filled grains, e.g. by means of paste-like components or the like, ensures that a defined structure is created which also further optimises constant and reproducible vaporizing conditions and provides a fixed sediment in particular for the event of electrical conductivity of the grains.

The preferred grain size is between 0.1 µm and 2 mm, particularly preferably between 3 µm and 300 µm. The advantages described above can be achieved particularly effectively with a grain size within these ranges.

The maximum grain size, depending on the flow property of the liquid to be conveyed in each case, expediently lies outside a magnitude which rules out capillary conveyance. In other words, the formation of microchannels within the wick member is ensured by the restriction of the maximum grain size in order to ensure in particular the—at least initially—capillary conveying flow of the liquid for a uniform and constant supply.

The grains of the wick body are advantageously composed of sand and/or graphite. These low-cost types of grain are almost freely available in nature and are chemically inert and environmentally friendly.

In one preferred further development, the grains of the wick member are at least partially magnetic. As a result of this, the grains can be oriented in a targeted manner in order to influence e.g. the flow resistance.

One particularly preferred embodiment is characterised in that the wick member and the heating member are separate units which bear against one another in a contact region, wherein the wick member faces the storage tank and the heating member faces the flow channel, and the heating member has electrical contacts for electrical contact with the energy source, and wherein the wick member has microchannels and the heating member, which is shielded off from the storage tank by the wick member, is formed to be liquid- and vapour-permeable. The microchannels in the wick member are formed in the manner described above by the grain arrangement and/or the grains themselves. The permeability of the heating member for liquid and gas or vapour can be formed e.g. by boring, lasering, etching or the like. In the case of this quasi "two-piece" formation of the vaporizer unit, each element itself can be optimally adapted to the respective functionality, namely the wick member in particular to the storage and conducting of the liquid out of the storage tank to the heating member, and the heating member in particular to taking over the liquid from the wick member and converting the liquid into gas or vapour and discharging it into the flow channel.

Due to the fact that the wick member is formed from granular grains, the wick member bears tightly and in a flat manner against the heating member. A uniform bearing of the wick member against the heating member is therefore ensured, as a result of which an optimised fluid coupling on the one hand and a homogeneous thermal link on the other hand are created. In the mounted/filled state, the wick member bears with an entry side in the direction of the storage tank in the liquid and with the exit side against the heating member. The heating member bears in turn with an entry side against the wick member and points with an exit side into the flow channel. A constant and homogeneous liquid supply of the heating member and thus reproducible vaporizing conditions are ensured with the preferred embodiment.

The heating member is advantageously a MEMS component (Micro-Electro-Mechanical-System) which is composed substantially of silicon or has silicon or p- or n-doped silicon and, proceeding from an upper side facing the wick member down to a lower side facing the flow channel, has liquid- and vapour-permeable passages. Particularly effective vapour formation can be achieved with this space-saving heating member.

The minimum grain size of the grains of the wick member at least in the contact region to the heating member is advantageously larger than the average diameter of the passages of the heating member. A blocking of the passages of the heating member is effectively prevented as a result of this.

In one preferred embodiment, the vaporizer cartridge comprises a housing which surrounds the hollow body and the vaporizer unit, wherein the housing wall delimits the storage tank towards the surroundings. A simple and installation space-saving design is thus ensured.

In one expedient variant, the housing wall holds the wick member in its position. A simple design is created as a result of the dual function of the housing wall as a delimitation for the storage tank and as a fixing means of the wick member within the receiving chamber.

The object is also achieved by an inhaler of the above-mentioned type in that the vaporizer cartridge is configured and adapted described herein.

The advantages which arise from this were already described in conjunction with the vaporizer cartridge, hence reference is made to the above statements to avoid repetition.

DESCRIPTION OF THE DRAWINGS

Further expedient and advantageous features and further developments in relation to the vaporizer cartridge and the inhaler are apparent from the subordinate claims and the description. Particularly preferred embodiments of the vaporizer cartridge and the inhaler are explained in greater detail on the basis of the enclosed drawing. In the drawing:

DETAILED DESCRIPTION OF THE PREFERRED EMBODIMENTS

Figure 1:
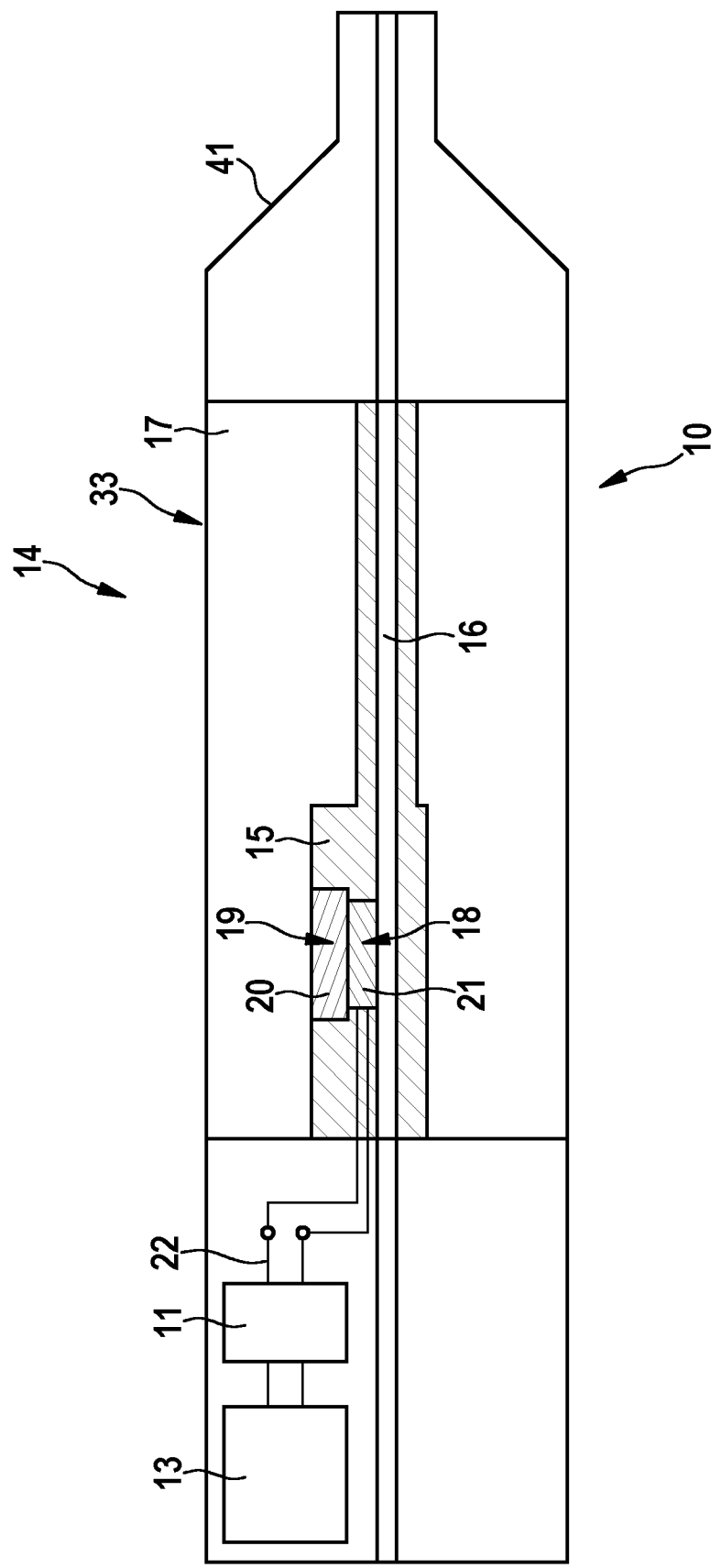
FIG. 1 shows a schematic representation of a preferred embodiment of an inhaler according to the invention with cartridge carrier and vaporizer cartridge in partial section.

The vaporizer cartridge represented in the drawing as well as the inhaler serve the purpose of inhalation of vapour enriched with active ingredients, e.g. nicotine, and/or aerosols from liquids and are correspondingly described in conjunction with an E-cigarette. The vaporizer cartridge and the inhaler can be used in the same manner to inhale vapour enriched with medical active ingredients from pharmaceutical products and/or food supplements.

The represented vaporizer cartridge 10 comprises a hollow body 15 with a continuous flow channel 16 as well as a storage tank 17 for storing liquid, wherein the storage tank 17 has at least one access opening 18 to the flow channel 16, and a vaporizer unit 19 extending over the entire access opening 18 is arranged in the region of each access opening 18, which vaporizer unit 19 has a wick member 20 and a heating member 21, wherein the vaporizer unit 19 is formed to be liquid-permeable in such a manner that liquid can be conveyed at least initially in a capillary manner from the storage tank 17 through the vaporizer unit 19 in the direction of the flow channel 16.

The hollow body 15 with its at least one flow channel 16, two or more flow channels 16 can likewise be provided, forms a suction channel/vent. The form of the hollow body 15 just like the profile of the flow channel 16 can be almost as desired. It is vital that the entry side $E_S$ of each flow channel 16 is open to the surroundings, in order e.g. to be able to take in air, and that the exit side $A_S$ is open in order to be able e.g. to generate a vacuum, in particular by the suction of a consuming person. Open means in this context that the entry side $E_S$ and the exit side $A_S$ are air-permeable. In the region of the access opening 18 between storage tank 17 and flow channel 16, the vaporizer unit 19 forms a type of liquid blockade which prevents liquid flowing directly out of the storage tank 17 and as liquid into flow channel 16. Irrespective of the form and formation of the storage tank 17, two or more storage tanks 17 can also be provided, and of the hollow body 15 and the arrangement/positioning of storage tank 17 to hollow body 15, the vaporizer unit 19 ensures that liquid is necessarily conducted out of the storage tank 17 in the direction of the flow channel 16 and at the latest when exiting from the vaporizer unit 19 is output as gas or vapour into the flow channel 16.

This vaporizer cartridge 10 is characterised according to the invention in that the wick member 20 is formed from a plurality of granular grains 24 which, as a result of their fill and/or formation, form microchannels 23. Grains 24 which lie against one another form on the one hand micro-cavities with adjacent grains 24, on the other hand, the grains 24 themselves can have micro-cavities, what are known as pores. As a result of the linking and the interaction of all the micro-cavities in the and between the grains 24, the microchannels 23 are formed which ensure an at least initially capillary conveyance and are formed continuously and have a non-linear profile. When passing through the vaporizer unit 19 comprising the wick member 20 and the heating member 21, during operation of the vaporizer cartridge 10, vapour and/or aerosol are formed from the liquid of the storage tank 17 towards the flow channel 16, wherein the porous structure of the wick member 20 on the one hand forms a storage medium for liquid and on the other hand represents a flow resistance. The direction of flow of the liquid occurs from the storage tank 17 through the vaporizer unit 19 in the direction of the flow channel 16.

The vaporizer cartridge 10 according to the invention can as a single-use article be a structural unit which contains the components hollow body 15, storage tank 17 and vaporizer unit 19. The vaporizer cartridge 10 can, however, also be formed in multiple parts, wherein components of vaporizer cartridge 10 are distributed to the single-use article and the multi-use article in such a manner that e.g. the storage tank 17 is a single-use article, which only leads to the structural unit of the vaporizer cartridge 10 upon combination with a cartridge carrier 13 that can be a multi-use article and can also comprise, in addition to an electronic control unit 11 and an energy source 12, components of the vaporizer cartridge 10, such as e.g. the hollow body 15 and the vaporizer unit 19. The vaporizer cartridge 10 is correspondingly defined via its components, namely hollow body 15 with flow channel 16, storage tank 17 and vaporizer unit 19, and not via the constructive/structural assignment of the components to the multi-use article or single-use article.

The features and further developments described below represent, as seen on their own or in combination with one another, preferred embodiments. It is expressly pointed out that features which are summarised in the claims and/or the description and/or the drawing or are described in a joint embodiment can also functionally independently further develop the vaporizer cartridge 10 described further above.

The wick member 20 has microchannels 23 which extend continuously from an entry side $E_D$ of the wick member 20 to an exit side $A_D$ of the wick member 20. In a first embodiment, the wick member 20 simultaneously forms the heating member 21 (see in particular FIG. 2). The wick member 20 thus forms the entire vaporizer unit 19. To this end, the granular material which forms the granular wick member 20 is at least partially electrically conductive. The electrically conductive grains 24 are preferably located at least in a lower region facing the flow channel 16. The electrical contacts 22 are correspondingly arranged in the electrically conductive region of the wick member 20. In this design, the microchannels 23 extend from the entry side $E_D$ of the wick member 20, which is exposed to the liquid in the storage tank 17, up to the exit side $A_D$ of the wick member 20 which directly adjoins the flow channel 16.

The vaporizer cartridge 10 is preferably configured and adapted for mechanical and electrical connection to the cartridge carrier 13 comprising at least the electronic control unit 11 and the energy source 12 for the formation of an inhaler 14, wherein the vaporizer unit 19 comprises electrical contacts 22 for electrical contact with the energy source 12. The inhaler 14 can be activated e.g. by an inhaling person, for example, as an E-cigarette, or e.g. by a pump, e.g. as a medical instrument in the event that the person himself or herself can no longer suck or not to an adequate extent.

Figure 2:
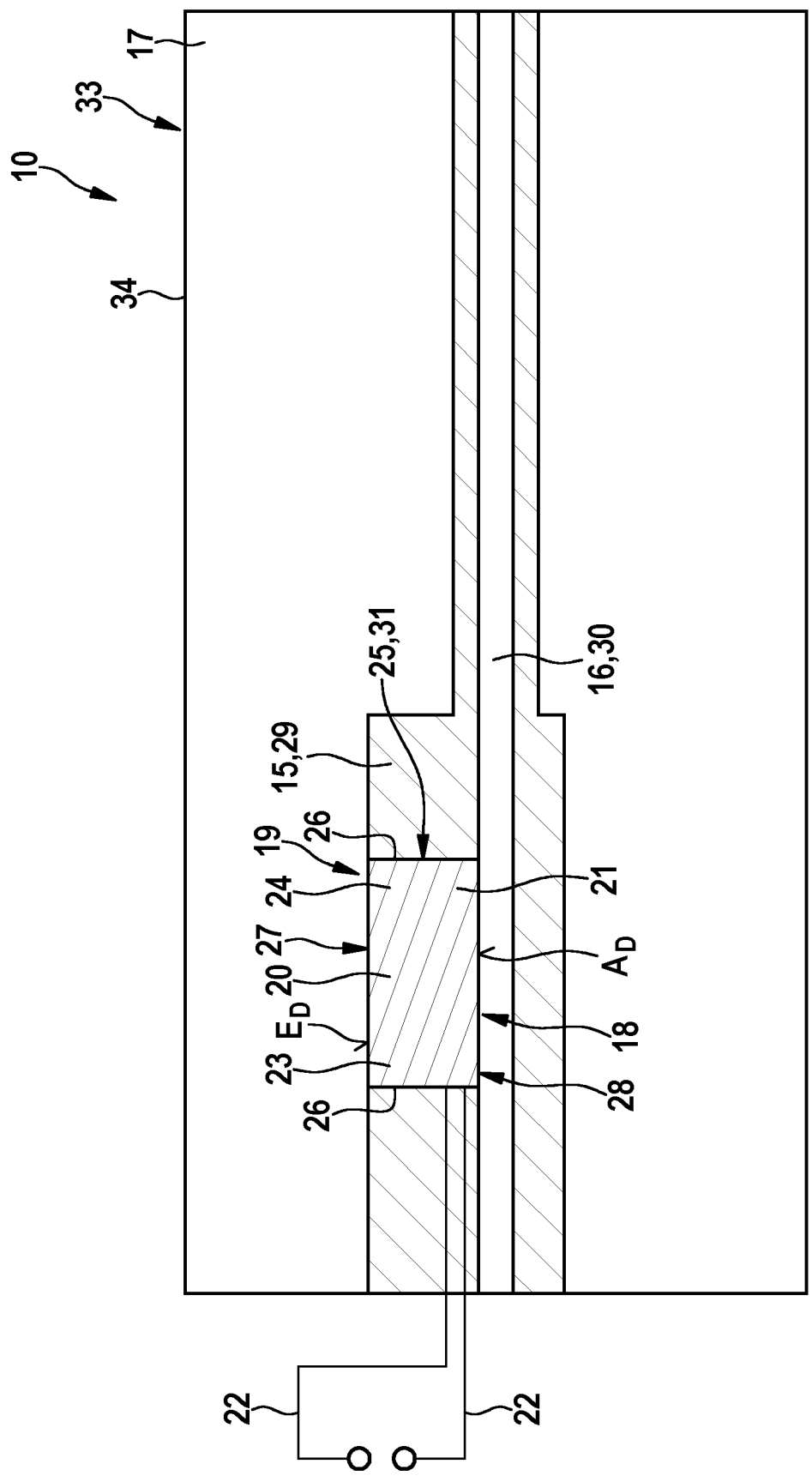
FIG. 2 shows an enlarged representation of a further embodiment of a vaporizer cartridge in partial section.
Figure 6:
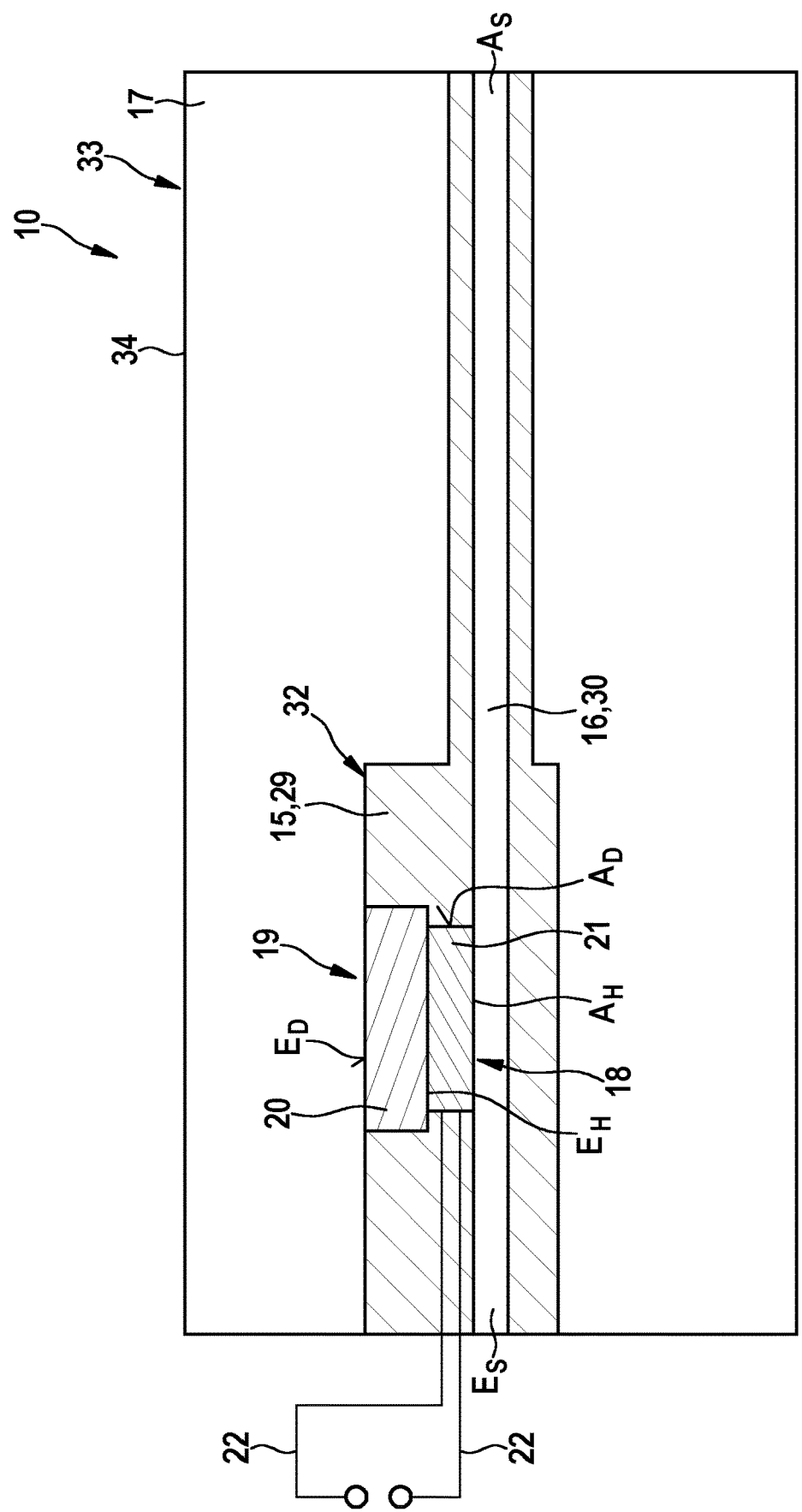
FIG. 6 shows an enlarged representation of the embodiment of the vaporizer cartridge according to FIG. 1 in partial section.

A receiving chamber 25 for receiving the vaporizer unit 19, in the example of FIG. 2 the wick member 20 and in the example of FIG. 6 the wick member 20 and the heating member 21 is formed in the region of the access opening 18, wherein the receiving chamber 25 for receiving liquid from the storage tank 17 into the vaporizer unit 19 and to discharge vapour from the vaporizer unit 19 into the flow channel 16 is at least partially delimited by a liquid- and gas- or vapour-permeable structure. The receiving chamber 25 for the vaporizer unit 19 can be formed by housing walls of other components of the vaporizer cartridge 10, by separate wall elements, projections, plates, covers, coil elements, valves or any other restriction or combinations thereof. The receiving chamber 25 can have any desired form and/or contour. In the example of FIGS. 2 and 6, the receiving chamber 25 is delimited e.g. circumferentially by wall elements 26. Directed towards the storage tank 17, the receiving chamber 25 with the vaporizer unit 19 located therein is covered, for example, by a cover element 27 which is formed to be liquid-permeable. Towards the flow channel 16, the receiving chamber 25 can be delimited e.g. by a liquid- and gas- or vapour-permeable grid structure 28 (see FIG. 2) or by a separate heating member 21 (see FIG. 6) which is correspondingly formed to be liquid- and vapour-permeable.

The vaporizer cartridge 10 preferably comprises a carrier element 29 which forms the hollow body 15 and on the one hand has a through-opening 30 for forming the flow channel 16 and on the other hand has a recess 31 for receiving the vaporizer unit 19. The carrier element 29 is preferably a tubular body. The recess 31 in which the vaporizer unit 19 is arranged is formed in the circumferential wall of the body. Unit formed from the carrier element 29 and the vaporizer unit 19 is preferably arranged within a housing 33 which forms the storage tank 17, wherein the inner volume of the storage tank 17 is formed between a housing wall 34 of the housing 33 and the carrier element 29. carrier element 29 can only extend partially through the housing 33 (see e.g. FIG. 2). In other embodiments, the carrier element 29 can also extend completely (see e.g. FIG. 6) through the housing 33.

The grains 24 can lie as a loose fill within the receiving chamber 25 or in the recess 31. In this case, even in the operating state of the vaporizer cartridge 10, the grains 24 can still move relative to one another and thus form variable microchannels 23. The grains 24 which lie next to one another and above one another are supported against one another. Grains 24 can strike against one another in a purely mechanical manner. The grains 24 can, however, also be mutually mechanically toothed with one another. It is correspondingly vital for the formation of the microchannels that the grains 24 bear against one another. In other embodiments, in particular in those in which the wick member 20 is simultaneously formed as heating member 21, the grains 24 within the receiving chamber 25 or in the recess 31 are at least partially connected to one another. Particularly preferably, a sediment formed from the granular and electrically conductive material is fixed in such a manner that the sediment forms a three-dimensional resistance heating matrix with parallel resistors and/or resistors connected in series. The electrical contacts 22 are formed or arranged on this resistance heating matrix. All of the means for fixing the grains 24 ensure a liquid coupling between the storage tank 17 and the heating member 21, optionally as a component of the wick member 20 or as a separate part.

The grains 24 of a wick member 20 can be formed to be identical and/or non-identical in terms of their material selection and/or their size. All grains 24 can have the same size, i.e. lie in a size range. The grains 24 can, however, different sizes, i.e. lie in different size ranges. The grain size is preferably between 0.1 µm and 2 mm and particularly preferably between 3 µm and 300 µm. Purely by way of example, all grains 24 can lie in a size range between 50 µm and 100 µm (corresponds to a size range). The grains 24 of a wick member 20 can, however, also have locally different grain sizes proceeding from the storage tank 17 in the direction of the flow channel 16. Layers of the wick member 20 close to the storage tank 17 can thus have grains 24 with a grain size of e.g. 200 µm to 300 µm (corresponds to a size range), while layers of the wick member 20 close to the flow channel 16 can have grains 24 with a grain size of e.g. 50 µm to 100 µm (corresponds to a size range). As a result of the selection of the grain sizes and the respective distribution e.g. in layers with grains 24 of different size ranges, among other things, the flow resistance of the wick member 20 can be set individually, ultimately even firstly during filling. As a result of the selection of the grain sizes used in a wick member 20, an individual pore gradient can be set for the wick member 20. The minimum grain diameter of the grains 24 in the fine-pore range should preferably be larger than the pores in the next roughest range in order to keep the pore gradient stable. The maximum grain size lies, depending on the flow properties of the liquid to be conveyed in each case, in each case outside a magnitude which rules out capillary conveyance. In other words, the grains 24 may only be of such a size that they still generate a capillary action as wick member 20. Equally, the grain diameter must not be smaller than the diameter of the capillaries or pores of the heating member 21 in order to prevent a blocking of the heating capillaries and/or an escape of the grains 24 out of the heating member 21.

All grains 24 can be composed of the same material. The grains 24 can, however, also be composed of at least two different materials. The grains 24 are preferably composed of sand (quartz) and/or graphite. Various other materials or mixtures of materials are, however, also possible as materials. Preferred materials for the grains 24 are e.g. PEEK granulate (polyetheretherketone granulate), PEK granulate (polyetherketone granulate), PA powder, VM17 granulate, glass, steatite, silicon dioxide, lignin, aerogel, viton, silicon, ash, charcoal, bentonite, zeolite, diatomite, magnesium silicate, hard spar, diatomaceous earth, ground porphyry as well as mixtures thereof. The grains 24 of a wick member 20 proceeding from the storage tank 17 in the direction of the flow channel 16 are particularly preferably composed locally of different materials. For example, a layered structure of the grains 24 composed in each case of the same material is understood as a local arrangement.

Various properties of the wick member 20 can be set by the selection of the materials of the grains 24 of a wick member 20. For example, grains 24 with different thermal conductivities can be used. Particularly preferably, the thermal conductivity of the grains 24 increases continuously or in steps or layers from the storage tank 17 in the direction of the flow channel 16. A layer with particularly high thermal conductivity can be formed e.g. in the border region to the flow channel 16, while a layer with only low thermal conductivity is formed in the direction of the storage tank 17. The different material selection of the grains 24 also leads to it being possible to form the grains 24 to be e.g. compressible. Depending on the magnitude of the contact pressure with which the grains 24 are retained e.g. in the recess 31 of the carrier element 29, the size of the pores of the individual grains 24 or adjacent grains 24 can be actively influenced by elastic deformation. The vaporizer cartridge 10 can optionally be assigned a control member, by means of which, in the operating state of the vaporizer cartridge 10, the contact pressure on the wick member 20 can be set. The control member can be e.g. a lever element, a rotary element or any other pressing means.

Multi-layer wick members 20 can also be formed. In one embodiment, a first layer can be formed with grains 24 of a first type of grain. A second layer is formed with grains 24 of a second type of grain. A third layer is again formed with the first type of grain. The grains 24 of the second type of grain in the middle layer have a specific property which can be detected e.g. by means of a micro-controller of the control unit 11. During operation of the vaporizer cartridge 10, for example, a change in the wetting of the grains 24 in the second layer leads to a detectable change in the specific property of the second type of grain. This change is detected via the micro-controller which can be e.g. a sensor. It is then possible to make a regulatory intervention into the vaporization process by means of the control unit 11 in order to prevent e.g. what is known as a dry puff of the heating member 21.

The grains 24 of the wick member 20 can have the same or different geometrical forms. The grains 24 can be, for example, needle-shaped, spherical, in the form of a grain of rice or also triangular. The grains 24 can have rounded edges or be formed with sharp edges. The term "grains" expressly does not refer to fibrous elements, i.e. does not refer to thin, fine, thread-shaped structures. For example, longitudinal and/or spherical pores can be formed depending on the respective form of the grains 24 and their grain size. The pores can also be formed to be irregular. The grains 24 can also be at least partially magnetic. As a result of this, the grains 24 can be aligned e.g. during filling/pouring into the receiving chamber 25 or the recess 31 by applying an external magnetic field in desired orientations. With the possibility of the alignment of the grains 24, for example, needle-shaped grains 24 can be oriented perpendicular to the flow channel 16, the properties of the wick member 20 can be determined individually in order to be able to use the wick member 20 e.g. as a non-return valve or as a control valve.

In a further, particularly preferred further development, the wick member 20 and the heating member 21 are separate units which bear against one another in a contact region 35, wherein the wick member 20 faces the storage tank 17 and the heating member 21 faces the flow channel 16. In this variant, the heating member 21 has electrical contacts 22 for electrical contact with the energy source 12. Using the example of the embodiment according to FIG. 6, the "two-piece" vaporizer unit 19 formed from wick member 20 and heating member 21 is arranged in the recess 31 of the carrier element 29. The vaporizer unit 19 is laterally circumferentially bordered and retained by the wall elements 26 of the recess 31. The entry side $E_D$ of the wick member 20 points towards the storage tank 17. In order to prevent loose the grains 24 or the grains 24 connected to one another of the wick member 20 leaving their position/location, the wick member 20 is secured towards the storage tank 17. Securing can be performed in various ways. Mechanical securing, for example, by the cover element 27, is particularly simple. Chemical, electrostatic, pneumatic or magnetic securing means can, however, optionally also be used. All of the securing means are, however, formed to be liquid-permeable in the direction of the storage tank 17 and ensure the liquid coupling between the storage tank 17 and the heating member 21, which points with its exit opening $A_H$ towards the flow channel 16. The wick member 20 thus shields the heating member 21 from direct contact with the storage tank 17.

The wick member 20 has microchannels 23. The heating member 21 is formed to be liquid- and vapour-permeable. The wick member 20 can be configured and adapted in one of the embodiments described above. With its exit side $A_D$, the wick member 20 bears against the entry opening $E_H$ of the heating member 21 and forms the contact surface 35. The heating member 21 itself preferably has linear and/or non-linear passages which open into the flow channel 16. The heating member 21 can have a flat or curved formation or a formation shaped in a different manner. The heating member 21 is particularly preferably a MEMS component (Micro-electro-mechanical-system) which is composed substantially of silicon or has silicon or p- or n-doped silicon and, proceeding from an upper side facing the wick member 20 down to a lower side facing the flow channel 16, has liquid- and gas- or vapour-permeable passages. The minimum grain size of the grains 24 of the wick member 20 at least in the contact region 35 to the heating member 21 is larger than the average diameter of the passages of the heating member 21.

As described above, the vaporizer cartridge 10 comprises a housing 33 which surrounds the hollow body 15 or the carrier element 29 and the vaporizer unit 19, wherein the housing wall 34 delimits the storage tank 17 towards the surroundings. The housing 33 is preferably formed to be cylindrical or rod-shaped. The housing wall 34 can be arranged spaced apart from the wick member 20. In other embodiments, the housing wall 34 can hold the wick member 20 in its position. The storage tank 17 can also be formed independently and separately from the housing 33. Further embodiment of features relevant to the invention are described in FIGS. 3 to 5 and 7 to 12.

Figure 3:
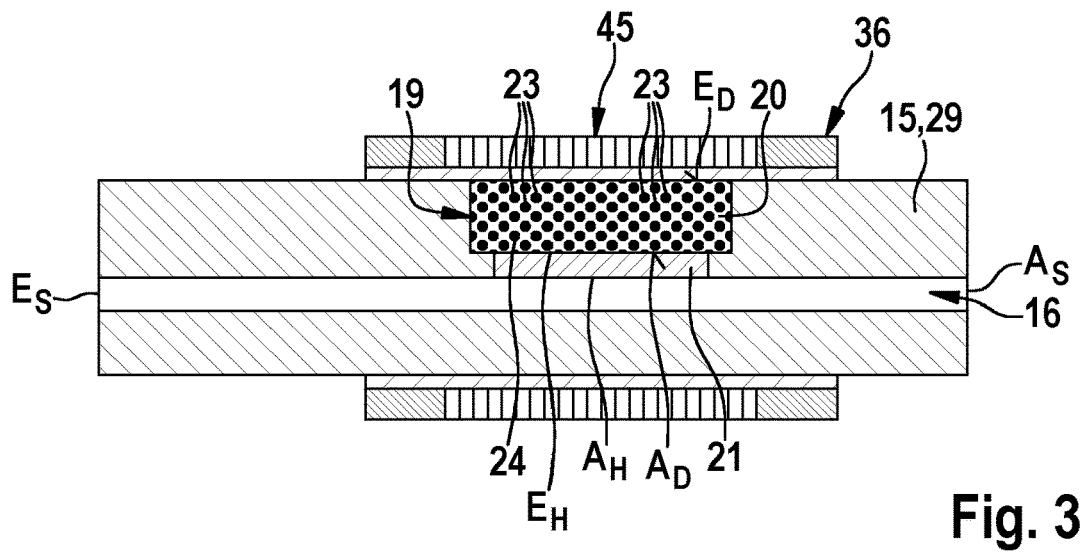
FIG. 3 shows an enlarged representation of a preferred embodiment of a part of a vaporizer cartridge in section.
Figure 4:
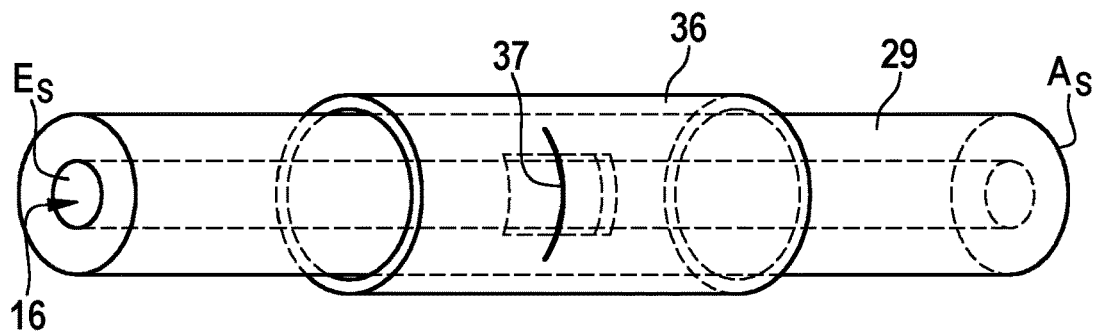
FIG. 4 shows a further embodiment of a part of a vaporizer cartridge.
Figure 5:
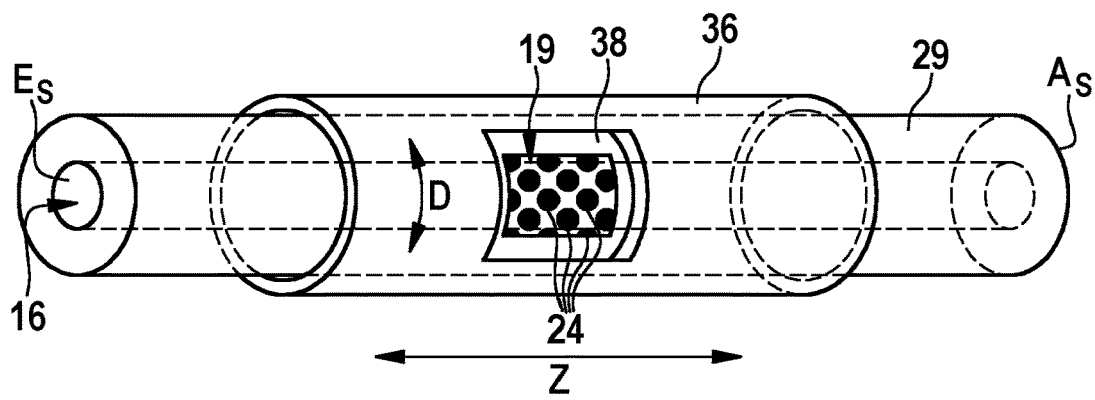
FIG. 5 shows a further embodiment of a part of a vaporizer cartridge.

FIG. 3 represents, for example, a tubular carrier element 29 with a continuous through-opening 30 which bears the two-piece vaporizer unit 19 in the recess 31. The vaporizer unit 19 is held in the recess 31 by an elastic sleeve 36 which is formed to be liquid-permeable at least in the region of the wick member 20, for this purpose the sleeve 36 can have e.g. a perforation 45. Instead of the elastic sleeve 36, for example, a (wrap of fleece material can also be used. FIGS. 4 and 5 represent in each case a tubular carrier element 29 in the case of which the vaporizer unit 19 is likewise held in position by an elastic sleeve 36. In FIG. 4, the sleeve 36 covers the wick member 20. The sleeve 36 has, however, a slit 37 which opens by pulling (see arrow Z) on the sleeve 36 to a window 38 (see FIG. 5) in order to release the wick member 20. Instead of the slit 37, in principle, the window 38 can be provided which can be moved by rotation (see arrow D) of the sleeve 36 out of a position in which the sleeve 36 covers the wick member 20 into a position in which the window 38 lies above the wick member 20.

Figure 7:
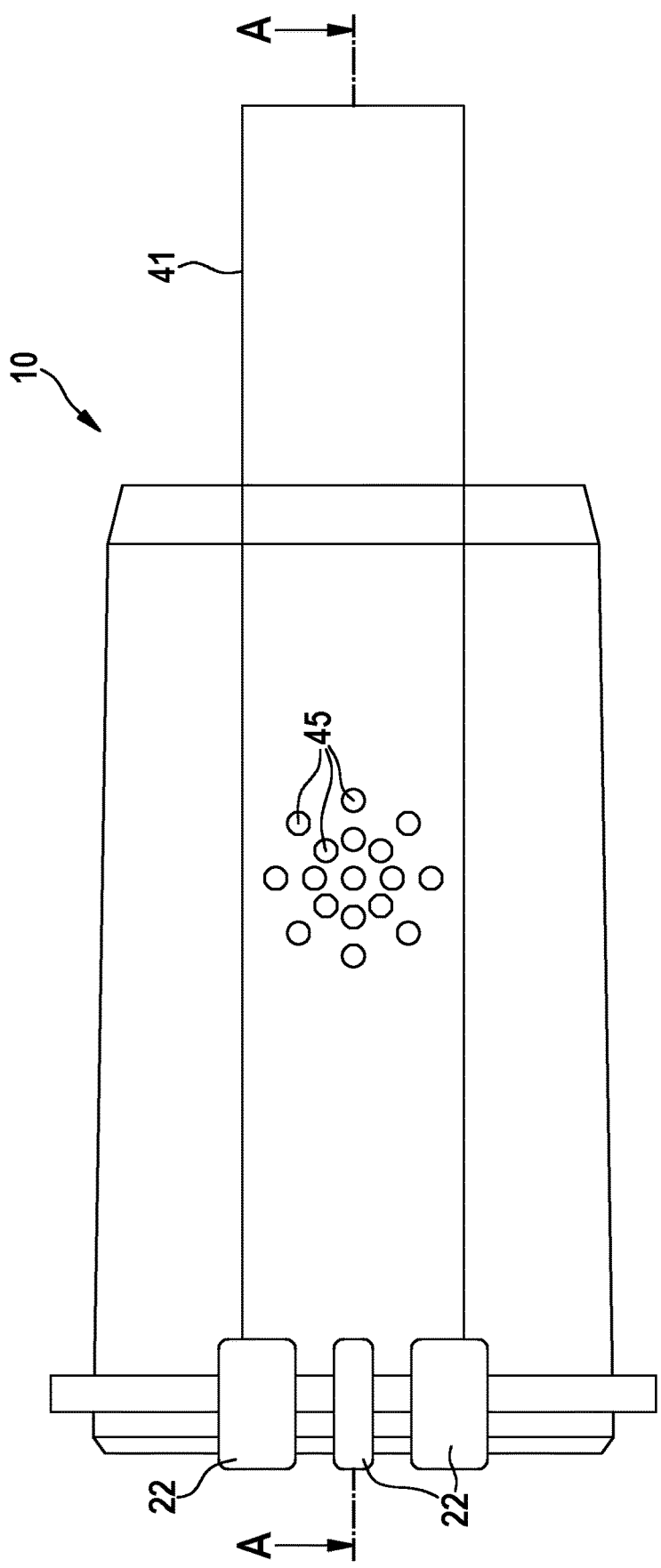
FIG. 7 shows an enlarged representation of a further embodiment of a part of a vaporizer cartridge.
Figure 8:
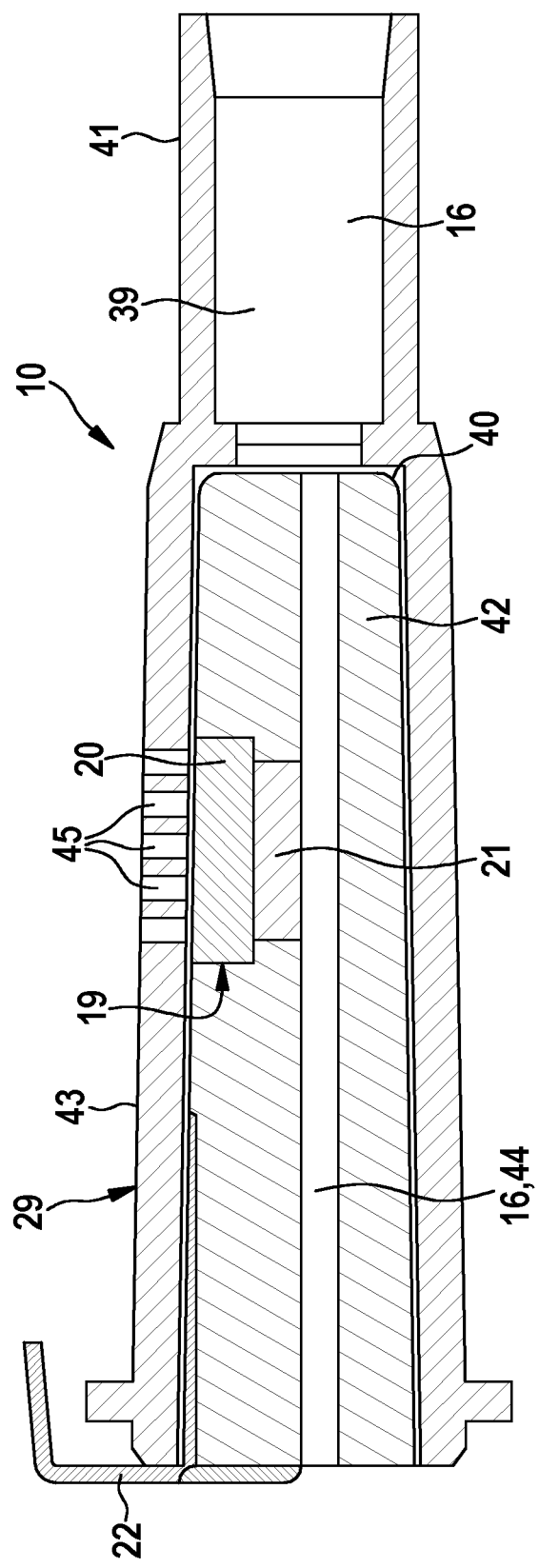
FIG. 8 shows the vaporizer cartridge according to FIG. 7 along section A-A.

FIGS. 7 and 8 show an embodiment in the case of which the carrier element 29 is formed to be tubular, wherein two chambers 39, 40 connected to one another are formed within the through-opening 30. A chamber 39 serves as mouthpiece 41. An insert 42 which bears the vaporizer unit 19 with the heating member 21 and the wick member 20 is arranged in the second chamber 40. The vaporizer unit 19 is "clamped", i.e. held in position between the insert 42 and the inside of a wall 43 of the carrier element 29. The insert 42 furthermore has a through-opening 44 which is operatively connected to the first chamber 39 for the formation of the flow channel 16. The carrier element 29 has, in the wall 43 in the region against which the wick member 20 abuts on the inside of the wall 43 of the tubular carrier element 29, a perforation 45 which ensures a liquid coupling to the storage tank 17. The storage tank 17 is correspondingly formed between the housing wall 34 of the housing 33 and the wall 43 of the carrier element 29.

Figure 10:
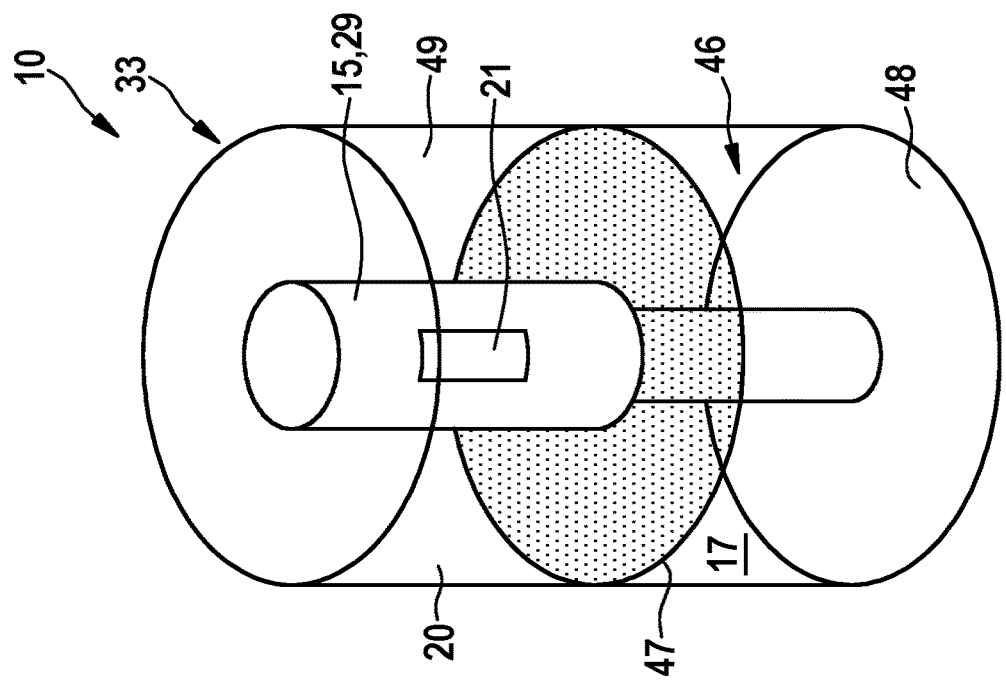
FIG. 10 shows the vaporizer cartridge according to FIG. 9.
Figure 9:
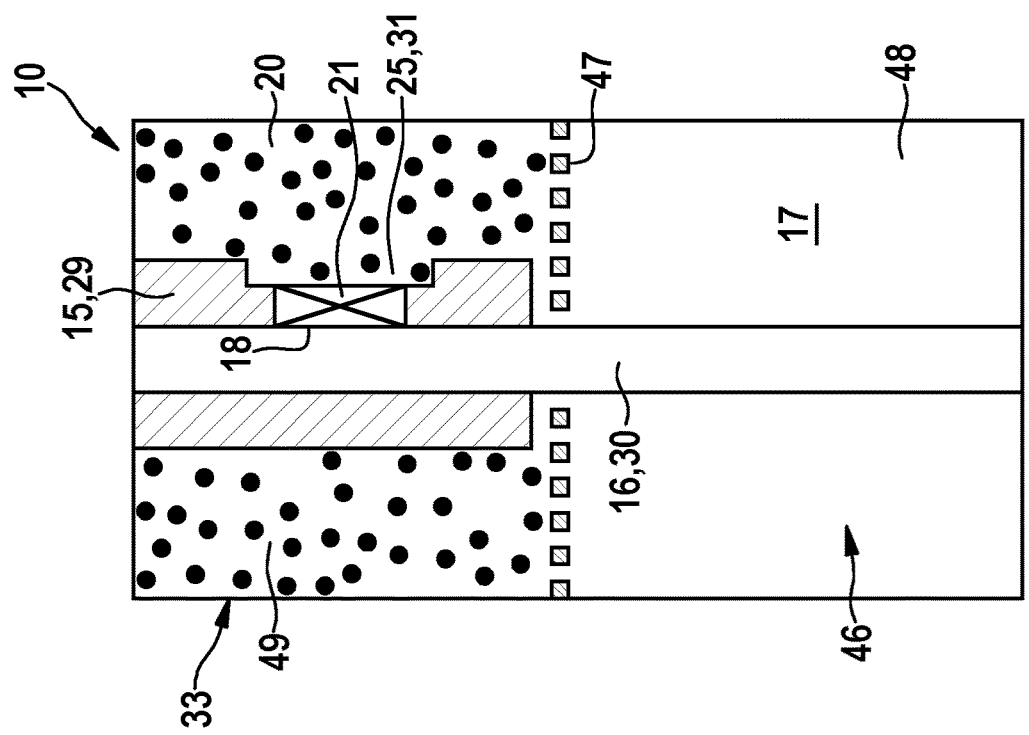
FIG. 9 shows an enlarged representation of a further embodiment of a vaporizer cartridge in partial section.
Figure 12:
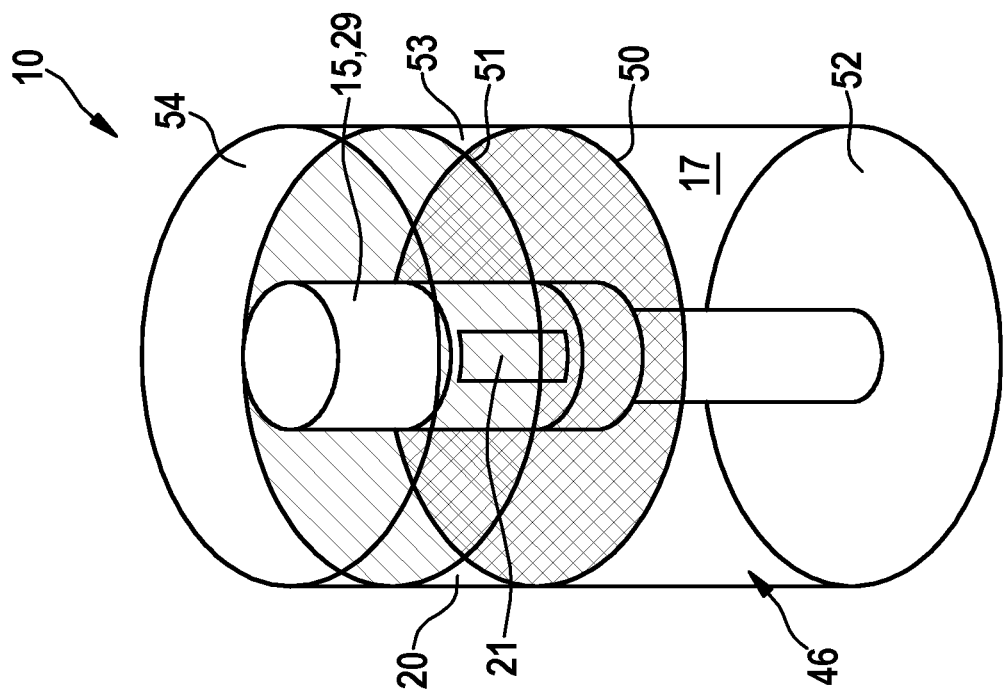
FIG. 12 shows the vaporizer cartridge according to FIG. 11.
Figure 11:
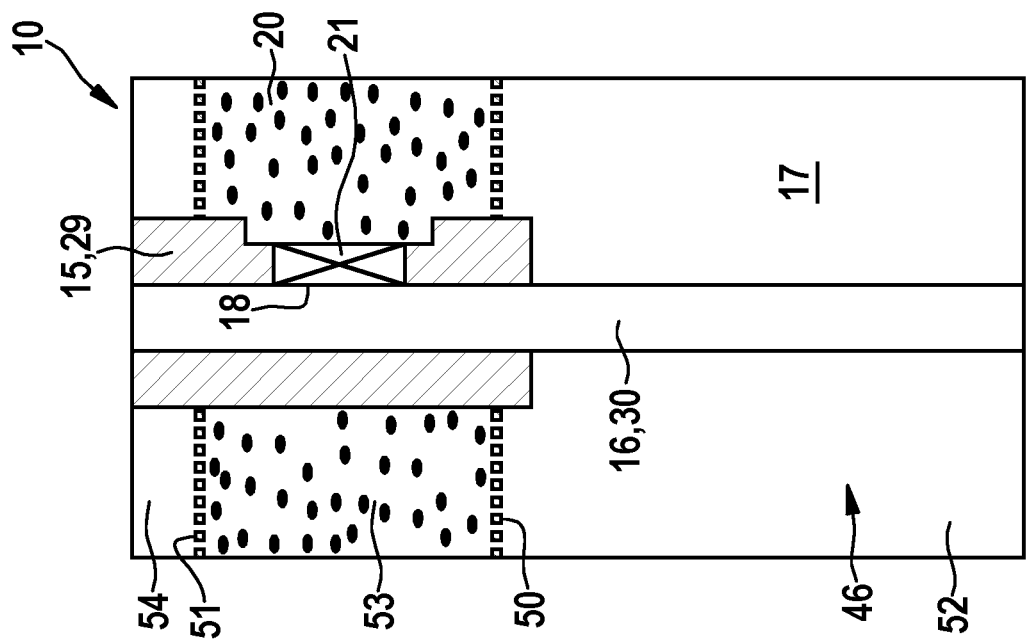
FIG. 11 shows an enlarged representation of a further embodiment of a vaporizer cartridge in partial section.

FIGS. 9 to 12 show further embodiments of possible vaporizer cartridges 10. In the case of these embodiments, a cylindrical housing 33 is provided to form an inner space 46 in which a continuous vent is provided as flow channel 16. The form of the housing 33 can, however, be as desired. The carrier element 29 extends over a part of the flow channel 16. The recess 31 in which the heating member 21 is arranged is formed in the carrier element 29. In the variant of FIGS. 9 and 10, a grid structure 47 divides the inner space 46 into two regions 48, 49, wherein one region 48 serves as the storage tank 17 for the liquid and one region 49 serves to receive the granular wick member 20. The grid structure 47 is arranged below the carrier element 29 in such a manner that the wick member 20 entirely surrounds the carrier element 29 and correspondingly also covers the heating member 21. In the variant of FIGS. 11 and 12, two grid structures 50 and 51 are provided which divide the inner space into three regions 52, 53, 54. Both grid structures 50, 51 are arranged above and below the recess 31 with the heating member 21 in such a manner that the centre region 53, which serves to receive the wick member 20, covers the carrier element 29 at least in the region of the heating member 21. Liquid can be stored in other regions 52, 54.

The functional principle of the inhaler 14 according to the invention which comprises a vaporizer cartridge 10 according to the invention is described by way of example on the basis of an E-cigarette as an inhaler 14 in particular in relation to FIG. 1. A consuming person sucks e.g. on a mouthpiece 41 of the inhaler 14 which is formed from the cartridge carrier 13 and the vaporizer cartridge 10, wherein a liquid which contains, for example, glycerine, propylene glycol and possibly further active ingredients and/or flavourings is located in the storage tank 17 of the vaporizer cartridge 10. As a result of the sucking, a vacuum is generated in the flow channel 16, which vacuum itself activates the control unit 11 e.g. via a sensor, not represented. The control unit 11 controls the heating member 21 which is supplied with energy by the energy source 12. Liquid from the storage tank 17 is transported by means of the wick member 20 at least initially in a capillary manner through the microchannels 23 out of the storage tank 17 in the direction of the heating member 21. At or in the heated heating member 21, the liquid is converted into gas or vapour, wherein the heating member 21 transports the liquid or the gas formed therefrom or the vapour formed therefrom as a result of the liquid- and gas- or vapour-permeable structure in the direction of the flow channel 16 and discharges it to said flow channel. The gas escaping from the heating member 21 mixes in the flow channel 16 with the air flow, wherein the actual recondensation/vapour formation process arises, and is sucked in and inhaled by the consuming person.

The invention claimed is:

1. A vaporizer cartridge as a component of an inhaler, comprising:
    a hollow body with a continuous flow channel;
    a storage tank for storing liquid, the storage tank having an access opening to the flow channel;
    a vaporizer unit arranged in a region of the access opening and extending over an entirety of the access opening, the vaporizer unit comprising a wick member and a heating member, wherein the vaporizer unit is formed to be liquid-permeable such that liquid is conveyed at least initially in a capillary manner out of the storage tank through the vaporizer unit in a direction of the flow channel;
    wherein the wick member is formed from a plurality of granular grains which form microchannels as a result of their fill and/or formation, and;
    wherein the grains lie as loose fill.

2. The vaporizer cartridge according to claim 1, wherein the microchannels extend continuously from an entry side of the wick member to an exit side of the wick member.

3. The vaporizer cartridge according to claim 1, wherein the vaporizer cartridge is configured and adapted for mechanical and electrical connection to a cartridge carrier, for the formation of an inhaler, the inhaler at least comprising an electronic control unit and an energy source, wherein the vaporizer unit comprises electrical contacts for electrical contact with the energy source.

4. The vaporizer cartridge according to claim 1, wherein the granular material which forms the granular wick member is at least partially electrically conductive.

5. The vaporizer cartridge according to claim 1, wherein a receiving chamber for receiving the vaporizer unit is formed in the region of the access opening, the receiving chamber for receiving liquid from the storage tank into the vaporizer unit and to discharge gaseous liquid/vapour from the vaporizer unit into the flow channel, the receiving chamber being at least partially delimited by a liquid- and gas- or vapour-permeable structure.

6. The vaporizer cartridge according to claim 1, wherein the vaporizer cartridge comprises a carrier element which forms the hollow body and, on the one hand, has a through-opening for forming the flow channel and, on the other hand, has a recess for receiving the vaporizer unit.

7. The vaporizer cartridge according to claim 4, wherein a sediment formed from the granular and electrically conductive material is fixed such that the sediment forms a three-dimensional resistance heating matrix with parallel resistors and/or resistors connected in series.

8. The vaporizer cartridge according to claim 1, wherein the grains of the wick member are formed to be identical and/or non-identical in terms of their material selection and/or their size.

9. The vaporizer cartridge according to claim 1, wherein the grains of the wick member, proceeding from the storage tank in the direction of the flow channel, have locally different grain sizes.

10. The vaporizer cartridge according to claim 1, wherein the grains of the wick member, proceeding from the storage tank in the direction of the flow channel, are composed locally of different materials.

11. The vaporizer cartridge according to claim 5, wherein the grains of the wick member are within the receiving chamber.

12. The vaporizer cartridge according to claim 1, wherein a grain size of the grains is between 0.1 µm and 2 mm or between 3 µm and 300 µm.

13. The vaporizer cartridge according to claim 1, wherein a maximum grain size of the grains, depending on a flow property of the liquid to be conveyed in each case, lies outside a magnitude which rules out capillary conveyance.

14. The vaporizer cartridge according to claim 1, wherein the grains of the wick member are composed of sand and/or graphite.

15. The vaporizer cartridge according to claim 1, wherein the grains of the wick member are at least partially magnetic.

16. The vaporizer cartridge according to claim 1, wherein:
    the wick member and the heating member are separate units which lie against one another in a contact region;
    the wick member faces the storage tank;
    the heating member faces the flow channel;
    the heating member has electrical contacts;
    the wick member has microchannels; and
    the heating member is shielded off from the storage tank by the wick member and is formed to be liquid- and vapour-permeable.

17. The vaporizer cartridge according to claim 16, wherein the heating member is a MEMS component (Micro-Electro-Mechanical-System) which is composed substantially of silicon or has silicon or p- or n-doped silicon and, proceeding from an upper side facing the wick member down to a lower side facing the flow channel, has liquid- and gas- or vapour-permeable passages.

18. The vaporizer cartridge according to claim 17, wherein a minimum grain size of the grains of the wick member at least in the contact region to the heating member is larger than an average diameter of the passages of the heating member.

19. The vaporizer cartridge according to claim 1, further comprising a housing which surrounds the hollow body and the vaporizer unit, wherein a housing wall of the housing delimits the storage tank towards surroundings.

20. The vaporizer cartridge according to claim 19, wherein the housing wall holds the wick member in position.

21. An inhaler configured and adapted for the inhalation of vapour enriched with active ingredients, comprising:
    a cartridge carrier at least comprising an electronic control unit and an energy source; and
    a vaporizer cartridge according to claim 1.

* * * * *